US006566068B2

(12) United States Patent
Rabbani et al.

(10) Patent No.: US 6,566,068 B2
(45) Date of Patent: *May 20, 2003

(54) PROCESS FOR DETECTING A NUCLEIC ACID OF INTEREST USING AN OLIGO- OR POLYNUCLEOTIDE PROBE AND INTERCALATORS

(75) Inventors: Elazar Rabbani, New York, NY (US); Ian Hurley, Staten Island, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/815,649

(22) Filed: Mar. 23, 2001

(65) Prior Publication Data

US 2001/0026921 A1 Oct. 4, 2001

Related U.S. Application Data

(63) Continuation of application No. 09/386,695, filed on Aug. 31, 1999, now Pat. No. 6,239,271, which is a continuation of application No. 08/486,053, filed on Jun. 7, 1995, now Pat. No. 5,998,135, which is a continuation of application No. 08/194,215, filed on Feb. 9, 1994, now abandoned, which is a continuation of application No. 07/314,995, filed on Feb. 24, 1989, now abandoned.

(51) Int. Cl.$^7$ ............................ C12Q 1/68; G01N 33/53

(52) U.S. Cl. ............................................. 435/6; 435/7.1

(58) Field of Search ..................... 435/6, 7.1; 436/94, 436/501

(56) References Cited

U.S. PATENT DOCUMENTS

| | | | |
|---|---|---|---|
| 4,257,774 A | 3/1981 | Richardson et al. |
| 4,547,569 A | 10/1985 | Letsinger et al. |
| 4,563,417 A | 1/1986 | Albarella et al. |
| 4,582,789 A | 4/1986 | Sheldon, III et al. |
| 4,637,988 A | 1/1987 | Hinshaw et al. |
| 4,670,572 A | 6/1987 | Hinshaw et al. |
| 4,707,352 A | 11/1987 | Stavrianopoulos |
| 4,707,440 A | 11/1987 | Stavrianopoulos |
| 4,711,955 A | 12/1987 | Ward et al. |
| 4,868,103 A | 9/1989 | Stavrianopoulos et al. |
| 4,921,805 A | 5/1990 | Gebeyehu et al. |
| 5,998,135 A | 12/1999 | Rabbani et al. |

FOREIGN PATENT DOCUMENTS

| | | |
|---|---|---|
| EP | 070685 A2 | 7/1982 |
| EP | 144914 A3 | 11/1984 |
| EP | 242527 B1 | 5/1992 |
| EP | 285057 B1 | 3/1995 |
| WO | WO8707955 | 6/1987 |

OTHER PUBLICATIONS

Horrocks, W.D. et al., *Journal of the American Chemical Society* 99(7):2378–2380 (1977).

Hemmilia, "Fluoroimmunoassays and immunofluorometric Assays", *Clin. Chem.* 31(3):359–370 (1985).

Gibson P.E., et al., "Detection of Human Polyomavirus DNA in Urine Specimens by Hybridot Assay," *Arch. of Virol.* 84:233–240 (1985).

Soini, E. and Kojola, H., "Time–Resolved Fluorometer for Lanthanide Chelates, A New Generation of Nonisotopic Immunoassays," *Clin. Chem.* 29(1):65–68 (1983).

Chun, P.K. et al., "Rapid Detection of Antigens Using Colloidal Gold in Membran Baed Immunoassays," from International Symposium on Rapid Methods and Automation in Microbiology and Immunology (5$^{th}$:1987:Florence, Italy), published in *Rapid Methods and Automation in Microbiology and Immunology*, Balows, A. et al., Editors, Brixia Academic Press Brescia, 572–577 (1989).

Syvanen et al., "Time–resolved fluorometry: a sensitive method to quantify DNA–hybrids,"*Nucleic Acids Research* 14(2): 1017–1028 (1986).

Dahlen et al., "Sensitive detection of genes by sandwich hybridization and time–resolved fluorometry,"*Molecular & Cellular Probes 1*: 159–168 (1987).

Kubota et al., "Fluorescence Decay And Quantum Yield Characteristics of Acridine Orange And Proflavine Bound to DNA, "*Biophysical Chemistry* 6:279–289 (1977).

Genest et al., "Investigation of DNA dynamics and drug–DNA interaction by steady state fluorescence anisotropy, "*Nucleic Acids Research* 13:2603–2615 (1985).

Asseline et al., "Oligodeoxynucleotides covalently linked to intercalating dyes as base sequence–specific ligands. Influence of dye attachment site,"*The EMBO Journal.* 3(4):795–800 (1984).

Wakelin & Waring, , "The Unwinding of circular Deoxyribonucleic Acid by Phenanthridinium Drugs: Structure–Activity Relations for the Intercalation Reaction", *Mol. Pharm.* 9:544–561 (1974).

(List continued on next page.)

Primary Examiner—Kenneth R. Horlick
(74) Attorney, Agent, or Firm—Ronald C. Fedus

(57) ABSTRACT

Disclosed is a nucleic acid hybridization assay composition for detecting the presence or absence of a target oligo- or polynucleotide in a sample. The composition comprises: a solid matrix having at least one surface which is substituted with a first intercalator capable of binding dsDNA, dsRNA, or DNA-RNA hybrids; a second intercalator, which may or may not comprise at least one fluorophore, said intercalator or said fluorophore, each acting as either an energy donor or an energy acceptor: and an oligo- or polynucleotide probe which is specifically hybridizable with the target oligo- or polynucleotide and has directly or indirectly bound thereto, at least one lanthanide metal chelate or at least one fluorophore, each acting as either an energy donor or an energy acceptor. Also disclosed are a method and kit for its use.

24 Claims, No Drawings

OTHER PUBLICATIONS

Wakelin & Waring, "Kinetics of Drug–DNA Interaction," *J. Mol. Biol.* 144:183–214 (1980).

Saenger W., *Principles of Nucleic Acid Structure*, pp. 116–58 Springer–Verlag, New York.

Syvanen, Nucleic Acid Hybridization: From Research Tool To Routine Diagnositic Method, *Medical Biology* 64:313–324 (1986).

Syvanen et al., Fast quantification of nucleic acid hybrids by affinity–based hybrid collection, *Nucleic Acids Research* 14(12):5037–5048 (1986).

Sommer, R. and Tautz, D., "Minimal homology requirements for PCR primers,"*Nucleic Acids Research* 17(16):6749 (1989).

Georghiou, "Interaction of Acridine Drugs With DNA And Nucleotides,"*Photochemistry and Photobiology* 26:59–68, Pergamon Press, Great Britain (1977).

Oser A. et al., "Sensitive non–radioactive dot–blot hybridization using DNA probes labelled with chelate group substituted psoralen and quantitative detection by europium ion fluorescence," *Nuc. Acid Research* 16(3):1181–1197 (1988).

PROCESS FOR DETECTING A NUCLEIC ACID OF INTEREST USING AN OLIGO- OR POLYNUCLEOTIDE PROBE AND INTERCALATORS

CROSS-REFERENCE TO OTHER RELATED APPLICATIONS

This application is a continuation of U.S. patent application Ser. No. 09/386,695, filed on Aug. 31, 1999, issued as U.S. Pat. No. 6,239,271 on May 29, 2001, which application is a continuation of U.S. patent application Ser. No. 08/486,053, filed on Jun. 7, 1995, issued as U.S. Pat. No. 5,998,135 on Dec. 7, 1999, which application is a continuation of U.S. patent application Ser. No. 08/194,215, filed on Feb. 9, 1994, abandoned, which is a continuation of U.S. patent application Ser. No. 07/314,995, filed on Feb. 24, 1989, also abandoned.

BACKGROUND OF THE INVENTION

1) Field of the Invention

The present invention relates to the field of hybridization assay methods, and more particularly, it relates to hybridization assay techniques in which the presence of an analyte is determined by means of energy transfer.

2) Brief Description of the Prior Art

Nucleic acid hybridization is an effective method for detecting and identifying pathogenic organisms and genetic disorders. It is also useful for mapping genes on chromosomes and in general has a wide spectrum of applications in clinical research. But despite the commercial availability of numerous target specific polynucleotide probes, detection or identification of infectious agents by hybridization is often not the preferred method. Instead, infectious agents are still cultured and identified by laborious, subjective and frequently inaccurate procedures.

Some of the commonly cited reasons for not using hybridization assays are the relative complexity of performing the assay procedure and the lack of sufficient sensitivity for detection or quantification when small numbers of the target organism are present. The most sensitive hybridization assays depend upon the use of radioisotopes for labeling the nucleic acid probe. However, the use of radioisotopes necessitates safety precautions and elaborate means for their disposal. In addition, radiolabels often have a short half-life (e.g., the half-life of $^{32}P$ is fourteen days), which makes their use expensive. Thus, it is recognized as being highly desirable to develop and improve nonisotopic hybridization detection methods.

At present, alternative methods are available which depend, inter alia either on the development of color or on the emission of fluorescence. Recently, highly sensitive time-resolved fluorescence (TRF) labeling, based on the long-lived emissions of lanthanide chelates, has been used in immunoassay and immunological detection of hybridization assay probes. Even though lanthanide ions, such as europium ($Eu^{+3}$) and terbium ($Tb^{+3}$) exhibit extremely weak luminescence when they are directly excited by visible light, it has been shown that these ions become highly fluorescent when they are chelated by organic ligands with good energy absorption properties. Absorption of the light by the ligand is followed by an efficient energy transfer from the excited ligand to the energy levels of the lanthanide ions. The fluorescence of lanthanide chelates is characterized by broad excitation in the absorption region of the ligand, a large Stokes' shift (>250 nm), narrow emission lines typical of the metal and an exceptionally long fluorescence lifetime (100–1000 μsec). See, Horrocks, W. D. et al., "Laser-Induced Lanthanide Ion Luminescence Lifetime Measurements by Direct Excitation of Metal Ion Levels, A New Class of Structural Probe for Calcium-Binding Proteins and Nucleic Acids," *Journal of the American Chemical Society* 99(7):2378–2380 (1977) and Hemmilia, clin. Chem., 31:359–370(1985).

In TRF assays, signals at the emission wavelengths of the lanthanide chelates are measured after a lapse in time between excitation and emission. This time-lag is sufficiently long to ensure that the specific long-lived fluorescence emissions of the lanthanide chelates are detected, but that the short-lived (<1 usec) background resulting from the intrinsic fluorescence of biological materials and other assay components (a serious problem in fluorometric measurements in biological samples) is not measured. This results in higher signal-to-noise ratios than are commonly observed in conventional fluorescence assays and consequently in an improvement in assay sensitivity.

Typically, TRF immunoassays are performed using $Eu^{+3}$ linked to antibodies via covalently bound chelators. After formation of the complex between the antigen and the antibody-chelate $Eu^{+3}$, the $Eu^{+3}$ in the complex is released, bound to suitable chelators such as those referred to above, then trapped in micelles. Pulsed light with an appropriate wavelength is applied to this micelle system. The resulting fluorescence is measured using a time resolving fluorometer. Under optimal conditions (i.e., high quality antibodies, stable chelation complexes, and suitable time resolving fluorometers), TRF immunoassays have the potential to exceed sensitivity levels obtainable with radioisotopic labels. See, Gibson, et al., Arch. of Virol., 84:233(1985).

TRF immunoassays with sensitivity levels comparable to radioimmunoassays using $^{125}I$ labels have been successfully used to measure levels of peptide hormones, alpha-fetoprotein, thyrotropin, choriogonadotropin and influenza viruses in clinical specimens. See, Hemmilia, supra; Soini and Kojola, Clin. Chem., 29:65(1983); Chun, P. K. et al., "Rapid Detection of Antigens Using Colloidal Gold in Membrane Based Immunoassays," from International Symposium on Rapid Methods and Automation in Microbiology and Immunology (5th) 1987, Florence, Italy, published in *Rapid Methods and Automation in Microbiology and Immunology,* Balows, A. et al., Editors, Brixia Academic Press, Brescia, pages 572–577 (1989).

Syvanen, et al., Nuc.Ac.Res. 14:1017(1986) have applied the technique of TRF immunoassays to the detection of DNA hybrids formed in sandwich hybridization assays. DNA probes carrying haptenic sulfone groups were hybridized to nitrocellulose-bound target DNA sequences (adenovirus genomic DNA). The hybrids were detected using a two-step antibody system. The first antibodies specifically recognized and became bound to the sulfone labels on the probe. The second antibodies consisted of sheep anti-rabbit IgG labeled with $Eu^{+3}$ by chelation. The $Eu^{+3}$ was released from this complex, chelated to diketones, trapped in micelles, and excited with UV light. The resulting emission was detected using a time resolving fluorometer. Syvanen et al. state that $Eu^{+3}$ can be bound to organic molecules by mediation of EDTA derivatives and that these chelates are unstable at hybridization conditions (data not shown), and that is the reason why the probe DNA cannot be directly labeled with Eu-EDTA chelates.

Two additional solid phase sandwich hybridization assays which employ TRF detection of hybridized probes and which are similar to the method described by Syvanen, et al., have been reported. Dahlen, et al., used streptavidin-Eu$^{+3}$, with the Eu$^{+3}$ attached to streptavidin through a diethylenetriamine pentaacetic acid (DTPA) chelator, to detect biotinylated probes in matrix-bound hybridization complexes. Dahlen, et al., Mol. & Cell. Probes 1:159(1987). In the sandwich assay developed by Oser, et al., DTPA was attached to poly-L-lysine groups which were covalently bound to probe DNA via psoralen linkages. The probes were labeled with Eu$^{+3}$ following hybridization. Nitrocellulose was used as the matrix in this system. Oser, et al., Nuc. Ac. Res., 16:1181(1988).

In both of these assays, as well as in the Syvanen, et al. assay, Eu$^{+3}$ was measured by TRF following its release from the hybridization-detection complex. Notwithstanding the high sensitivity of these reported TRF-DNA hybridization assays the length and complexity of these procedures make them unattractive for use in clinical laboratory settings. In addition, the lower detection levels of these assays are limited by high backgrounds resulting from the presence of measurable quantities of Eu$^{+3}$ in assay reagents, as well as in the environment (i.e., dust).

In another approach Sheldon III, et al., in U.S. Pat. No. 4,582,789, disclose a process for labeling nucleic acids with psoralen derivatives, which are also intercalators. A spacer arm chemically links the alkylating intercalation moiety with the label moiety, thereby allowing the label to react without interference, with detection means, such as antibodies.

Letsinger et al., U.S. Ser. No. 444,438, filed Nov. 24, 1982, now abandoned, is said by Sheldon et al., supra, to disclose bifunctional intercalators containing a phenanthridinium moiety as an agent for introducing markers (e.g., fluorescent probes) at specified regions in polynucleotides.

Albarella et al. in the European Publication 0,144,914 and in the U.S. Pat. No. 4,563,417 disclose a method of detecting a polynucleotide sequence, which is based, a priori, on a conventional antigen-antibody system. This method requires the formation of two complexes, the formation of a polynucleotide/polynucleotide complex, and the formation of an antigen/antibody complex. The target sequence is detected by means of an interaction between two labels. The preferred labeling pair is a pair of enzymes which interact sequentially to produce a detectable product. Another labeling pair which is disclosed, is one that involves energy interactions such as between a fluorescer or luminescer and a quencher for the photo-emission of the first label. Where the absorbing label is also a fluorescer, a second emission is the detectable signal.

Heller, et al in European Publication 0 070 685, published on Jan. 26, 1983, disclose a homogenous assay in which two single-stranded polynucleotide probes that are complimentary to mutually exclusive portions of the target polynucleotide, are used. In one embodiment of the assay, the first probe has an absorber/emitter moiety which absorbs a shorter wavelength of light than the absorber/emitter moiety on the second probe, but emits light in a wavelength region that overlaps with the absorbance region of the absorber/emitter moiety on the second probe. The absorber/emitter moiety used are combinations of fluorescent compounds, such as derivatives of fluorescein and rhodamine.

Use of a complex of lanthanide metal and a chelating agent comprising a nucleus which is a triplet sensitizer is disclosed by Hinshaw et al., U.S. Pat. Nos. 4,637,988 and 4,670,572.

Wiedner and Hale, in PCT Pub. No. WO87/07955 (filed Jun. 15, 1987), disclose a homogeneous assay which uses energy transfer as a means of detecting an analyte in very dilute solutions.

Stavrianopoulos et al., in European Publication No. 0242527 (published Oct. 28, 1987 and assigned to the instant assignee), disclose a homogeneous assay in which an energy transfer system for detection of the analyte is utilized. The energy donor or the energy acceptor can be either a fluorescent aromatic agent or a lanthanide metal. EP 0 242 527 is based upon the priority document, U.S. patent application Ser. No. 831,250, filed on Feb. 19, 1986, which issued as U.S. Pat. No. 4,868,103 on Sep. 19, 1989.

SUMMARY OF THE INVENTION

The present invention provides a nucleic acid hybridization assay composition for detecting the presence or absence of a target oligo- or polynucleotide in a sample. The composition comprises: a solid matrix having at least one surface which is substituted with a first intercalator capable of binding dsDNA. dsRNA or DNA-RNA hybrids, a second intercalator, which may or may not comprise at least one flurophore, said second intercalator or said flurophore, each acting as either an energy donor or an energy acceptor; and an oligo- or polynucleotide probe which is specifically hybridizable with the target oligo- or polynucleotide and has directly or indirectly bound thereto at least one lanthanide metal chelate or at least one fluorophore, each acting as either energy donor or an energy acceptor.

The invention further provides a nucleic acid hybridization assay method for detecting the presence or absence of a target oligo- or polynucleotide in a sample. This method begins by contacting a sample suspected of containing the target of interest with an oligo- or polynucleotide which is specifically hybridizable with the target and has directly or indirectly bound thereto at least one lanthanide metal chelate or at least one fluorophore each acting as either an energy donor or an energy acceptor; permitting hybridization of the target and the oligo- or polynucleotide which is specifically hybridizable therewith to form a complex; contacting the complex with (i) a solid matrix having at least one surface which is substituted with a first intercalator capable of binding dsDNA, dsRNA or DNA-RNA hybrids and (ii) a second intercalator, which may or may not comprise at least one fluorophore, said second intercalator or said fluorophore, each acting as either an energy donor or an energy acceptor; and detecting any energy emitted from the energy donor.

The invention also provides a nucleic acid hybridization assay kit comprising, in packaged combination, reagents for detecting the presence or absence of a target oligo- or polynucleotide in a sample.

The present invention offers a number of significant advantages over previously available methods. The use of the intercalator-bound solid matrix of the invention which serves to capture and concentrate the duplexes formed between the target polynucleotide and the probe allows hybridization to proceed in liquid. Formation of nucleic acid hybrids, whether DNA/DNA, RNA/RNA or RNA/DNA, proceeds with significantly more rapid rates when both interacting species are present in solution, as opposed to one species being attached to a solid matrix.

Also, because the detection complex is on a surface, it is more completely and precisely localized than it would be if it were in solution and therefore, the signal that is generated can be made much stronger by increasing the photon density of each laser pulse through focusing the laser beam onto the appropriate spot. The increased photon density increases the chance of exciting each donor molecule. This increase in the number of exited donors per pulse increases the chance that the acceptor will be excited in its turn and give off a photon to be detected.

In one embodiment of the invention, a very important advantage is the use of intercalating agents with different excitation optima. When the sample is energized at a wavelength which excites only the energy donor intercalator, but not the intercalator which serves to capture the hybrid, background emission is reduced, subsequently resulting in a more accurate quantitative determination of the target polynucleotides.

The TRF assay of the invention is more rapid and easier to perform than the complicated and lengthy assays so far available, in which overnight hybridization is often required, followed by antibody equilibration and washing steps before detection (see, e.g., Syvanen et al., supra).

DETAILED DESCRIPTION OF THE INVENTION

The following terms as used in the specification and claims hereof have the following meanings.

The term "sample" refers to those materials on which tests are performed, and includes biological, physiological, industrial, environmental and other types of solids and liquids. Of particular interest are biological tissues such as organ or musculoskeletal specimens or biopsies, cervical and peritoneal specimens or lavages and the like and fluids such as serum, plasma, urine, cerebrospinal fluid, saliva, milk, broth, and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluids which are tested by conventional methods are also encompassed by this term and can be assayed in accordance with the invention.

The terms "oligo- or polynucleotide target" or "target" refer to any nucleic acid-containing substance whose presence or absence is to be qualitatively or quantitatively determined in a sample. The assay of the present invention can be applied to the detection of target oligo- or polynucleotides which are at least partially present in single-stranded form or can be made at least partially single-stranded. The analyte, in functional terms, is usually selected from a naturally occurring or synthetic RNA or DNA for which a complementary nucleic acid exists or can be prepared.

The terms "oligo- or polynucleotide probe" or "probe" refer to any nucleic acid-containing compound or composite capable of recognizing a particular nucleic acid sequence in preference to other substances. In the majority of embodiments, the probes will be DNA hybridization assay oligonucleotide probes, such as those specific for disease-causing organisms, e.g., N. gonorrhoeae or human papilloma virus, or for identification of genetic disorders, e.g., Tay-Sach's disease or Down's syndrome.

The terms "linkage group", "linker arm", "linker" and the like refer to any of the well known bonds or compounds useful in joining functional groups and which do not substantially interfere with the characteristic properties or functions of the functional groups so joined. Examples of linkage groups which are useful in the present invention include those described for this purpose in Ward, et. al., U.S. Pat. No. 4,711,955: Stavrianopoulos, U.S. Pat. No. 4,707,352 and Stavrianopoulos, U.S. Pat. No. 4,707,440.

The terms "intercalating moiety" or "intercalator" refer to those compounds capable of non-covalent insertion between the base pairs of a nucleic acid duplex and are specific in this regard only to double-stranded (ds) portions of nucleic acid structures including those portions of single-stranded nucleic acids which have formed base pairs, such as in "hairpin loops". The nucleic acid structures can be dsDNA, dsRNA or DNA-RNA hybrids.

It is well known that certain fluorescence-emitting dyes have the ability to become inserted noncovalently or intercalated between bases in the double-stranded helix. For example, 9-aminoacridine, a planar, heterocyclic molecule, is one such compound. Ethidium bromide, a phenanthridine dye, is another such intercalating agent. Publications describing the use of intercalating dyes in studies using nucleic acids include Georghiou, Photochemistry and Photobiology, 26:59–68, Pergamon Press (1977); Kubota, et al., Biophys. Chem., 6:279–284 (1977); Genest, et al., Nuc. Ac. Res., 13:2603–2615 (1985); Asseline, EMBO J. 3: 795–800 (1984); Richardson, et. al., U.S. Pat. No. 4,257, 774; and Letsinger, et. al., U.S. Pat. No. 4,547,569.

A phenanthridine dye, 6-(-4'-carboxyphenyl)-3,8-diamino-5-methyl phenanthridinium chloride from May and Baker Ltd. London, England (M-B 3492), has been shown to bind to and unwind closed circular double-stranded DNAs almost identically as the prototypical intercalcator, ethidium. See, Wakelin and Waring, Mol. Pharm., 9:544–561 (1974). A temperature Jump. study of the M-B 3492-DNA system confirmed that binding occurs by intercalation. See, Wakelin and Waring, J. Mol. Biol., 144:183–214 (1980).

The time resolved fluorescence (TRF) hybridization assay of the present invention is based in part on the above-described property of intercalation of specific compounds between the bases of the double-stranded nucleic acid helix. The principal feature of this invention is the use of two different intercalators, one of which serves to capture or fix the double-stranded hybrid which is formed between the target polynucleotide and the labeled polynucleotide probe, to a solid surface and a different intercalator, which can act as, an energy donor, or as an energy acceptor, or has attached thereto, a fluorescent compound which serves as either the energy donor or the energy acceptor. The polynucleotide probe is labeled with either chelated lanthanide metals or fluorescent compounds, which serve as either energy donors or energy acceptors. The compounds chosen to serve as energy donors and energy acceptors must be such that transfer of energy can occur efficiently from a compound emitting energy at a first wavelength to a compound which absorbs energy at or near that wavelength and emits time-delayed or time-prolonged detectable energy at a second wavelength. For a further discussion of suitable energy transfer pair combinations, see the European Publication No. 0242527, supra;, which publication is referred to above is based upon the priority document, U.S. patent application Ser. No. 831,250, filed on Feb. 19, 1986, which issued as U.S. Pat. No. 4,868,103 on Sep. 19, 1989. The disclosure of U.S. Pat. No. 4,868,103 is herein incorporated by reference.

As stated above, the use of the intercalator-substituted solid matrix is solely for the purpose of capturing and concentrating nucleic acids in double-stranded form. The solid matrix is not used for attaching either the target or the analyte, which is often the case in conventional assays, and where hybridization then proceeds in two phases. In the method of the invention, hybridization takes place between the target and the probe in solution, in which it occurs much more rapidly, as compared to the situation where one of the reactants is bound to a solid surface.

In the case where the intercalators serve both in the capture and in the energy transfer functions, the characteristic fluorescence emission of the intercalators used must be of different wavelengths, so that upon irradiation of the sample, energy transfer will occur only from the second intercalator. This avoids, or reduces, or eliminates background emission or quenching which otherwise would occur if the wavelength of excitation chosen were to be identical to that of the capture intercalator.

One preferred embodiment of the time-resolved fluorescence (TRF) assay is as follows. The sample containing the analyte of interest is solubilized and its DNA denatured. An aliquot thereof is then dispensed into a well, such as in a microscope slide, and covered with a cover slip, the surface of which has been derivatized with an intercalating agent. The derivatization typically involves first adding reactive amino groups to an acid-washed glass surface. The surface is then reacted with an intercalator which is derivatized with a linkage group that terminates in a substituent capable of reacting with amino groups. A preferred linkage group consists of six or more atoms.

The well also contains an excess of the analyte-specific moiety, which comprises a polynucleotide probe labeled with a lanthanide metal, and reagents necessary for efficient hybridization and stable chelation of the lanthanide metal to the probe.

Hybridization is allowed to proceed for 10–60 minutes, under conditions of salt, denaturation and temperature, such that hairpin structures in analytes or probes are prevented from being formed. See e.g., W. Saenger (1984) "Principles of Nucleic Acid Structure", pp. 116–58, Springer-Verlag, New York. In the preferred embodiment, one or more washing steps are used to remove the excess probe strand which is tonically associated with the solid matrix. The washing steps are not necessary, but are preferred for greater accuracy, in order to avoid any energy transfer between the capture intercalator and the probe strand, thus leading to a production of non-specific signal. The washing steps are carried out under the same conditions as used for hybridization. A suitable energy donor, which is a different intercalating compound, is added in a room temperature phosphate buffer (>10 millimolar) following the washes. The energy acceptor is a lanthanide metal. It can be any metal of this series which has the desired fluorescence. It is usually either terbium ($Tb^{+3}$) or europium ($Eu^{+3}$). The glass slides are thus derivatized by one intercalating agent which serves to immobilize the analyte:analyte-specific moiety duplex while another intercalating agent, in solution, serves as the energy donor.

Any intercalating compounds can be used in this embodiment, as long as the pair used in the capture of the hybrid and as the energy donor have different excitation optima. Some intercalators which can be used in the capture of the hybrid are the psoralenamines, specifically, 8-[[[(diethylamino)methyl]propyl]oxy]psoralen, 5(N-piperadinyl)-8-methoxypsoralen, which is derivatized with linkers which contain secondary or tertiary amino groups or quartenary ammonium salts; phenanthridine dyes, such as ethidium bromide and 6-(-4'-carboxyphenyl)-3,8-diamine-5-methyl phenanthridinium chloride (M-B 3492).

Intercalators which can be used as energy donors include the acridine dyes, such as 9-aminoacridine, and the coumarins, for example, 7-hydroxy-4-methylcoumarin, 7-amino-4-methylcoumarin and 4-methyl-7-sulphatomethylcoumarin.

The preferred intercalator used in the capture of the hybrids is M-B 3492. The preferred energy transfer pair is the intercalator 9-aminoacridine as the donor and $Eu^{+3}$ as the acceptor.

The polynucleotide probes carrying the chelated metal label are prepared as described in Stavrianopoulos, U.S. Pat. No. 4,707,440 and assigned to the instant assignee. The disclosure of this patent is herein incorporated by reference. As is more fully described therein, the chelator is attached to the polynucleotide sequence of the probe through a linkage group, or "linker arm", such that this attachment does not substantially interfere with the hybridization of the polynucleotide. The base moiety, to which it is preferably attached, can be a purine or pyrimidine. Preferred linkage groups include those having an allylamine moiety. Preferred chelators include diethylenetriamine pentaacetic acid (DTPA) and trans-diaminocyclohexane tetraacetic acid (DCTA).

In other embodiments of this invention, the intercalator is not part of the energy transfer system, but comprises one or more fluorophores that act as either the energy donors or energy acceptors. The intercalator can be any substance, as long as it is different from the capture intercalator. Such an intercalator can be, for example, any one of the psoralenamines listed above and the energy donor, can be a naphthalene sulfonamide. M-B 3492 can also serve as an intercalator which comprises e.g., a pyrene compound that serves as the energy donor.

The fluorophores or the fluorescent energy compounds can be attached to the intercalator by any of a number of linkages or linker arms. Such linker arms are well known in the art and are described in Ward, U.S. Pat. No. 4,711,955 and in Stavrianopoulos, U.S. Pat. No. 4,707,440.

The fluorescent energy donor compound can also be a chelated lanthanide metal, when the probe is labeled with either a non-lanthanide fluorescent compound or is labeled with a lanthanide metal that is different from the metal which is serving as the energy donor.

Polynucleotide probes can also be labeled with fluorescent energy acceptor compounds that are not lanthanide metals. Such energy acceptors can be fluorescein, Texas Red, Rhodamine B and other fluorescent compounds. These compounds can be attached to polynucleotide probes via linkages, also well known in the art. See, e.g., Engelhardt et al., European Publication No. 0,285,057, published on Oct. 5, 1988 and assigned to the instant assignee. EP 0 285 057 is based upon the priority document, U.S. patent application Ser. No. 06/391,440, filed on Jun. 23, 1982, which was abandoned in favor of U.S. patent application Ser. No. 07/674,352, filed on Nov. 21, 1984, which in turn was abandoned in favor of U.S. patent application Ser. No. 07/140,980, filed on Jan. 5, 1988. U.S. patent application Ser. No. 07/532,704 was filed on Jun. 4, 1990 as a divisional application of the aforementioned Ser. No. 07/140,980, and issued as U.S. Pat. No. 5,241,060 on Aug. 31, 1993. This publication is herein incorporated by reference.

Detection of hybrid formation is accomplished using a fluorometer, preferably a novel TRE fluorometer, which is more fully described in commonly assigned U.S. patent application Ser. No. 07/304,748, filed on Jan. 31, 1989, which issued as U.S. Pat. No. 5,061,076 on Oct. 29, 1991, the disclosure of which is incorporated herein, by reference.

The following example illustrates but is not a limitation of the invention.

EXAMPLE 1

In this example, the first intercalator the phenanthridine dye M-B 3492, is used to capture the double-stranded target-probe hybrid to the surface of the slide and a second intercalator, 9-aminoacridine, is used in solution as the energy donor.

Slide Preparation

The glass coverslip surface is simultaneously methylated and aminopropylated at a ratio of 1 aminopropyl group per 100 methyl groups as follows. Fifteen fused silica microscope coverslips (2.2 cm×2.2 cm×0.8 mm) are boiled in 5M nitric acid for two hours then dried at 105° C. for 24 hours. They are then heated (118+2° C.) overnight in a covered evaporating dish containing aminopropyltriethoxysilane (13 μl), methyltriethoxysilane (2.9 ml) and xylene(22.5 ml). The coverslips are then removed, washed twice with water (10 ml) and allowed to air dry at room temperature.

The glass surfaces are then nitrobenzylated as follows. Ten of the coverslips treated as described above are placed in methylenetrichloride (10 ml) containing triethylamine (10 ml). Then, p-nitrobenzylchloride (100 mg) is added, the mixture is heated to 60° C. and maintained at that temperature overnight. The coverslips are washed three times in methylenetrichloride (10 ml) and air dried.

The glass surfaces are then diazotized as follows. Five of the coverslips treated as described above are introduced into 10% sodium hydrosulfite in water (10 ml) and heated to 100° C. for 30 minutes. The solution is removed while still hot and the coverslips are washed three times in sodium acetate buffer (10 ml) and twice in deionized water (10 ml). The coverslips are then transferred to a tube containing $NaNO_2$ (25 g) in cold 2M HCl (10 ml). This tube is supported in a beaker (250 ml) of ice to maintain a temperature of 0° C. The beaker containing the tube is placed in a dessicator connected to a water aspirator and maintained at low pressure for 20 minutes. The coverslips are then washed three times with cold 0.15M acetic acid (10 ml) and stored immersed in this liquid at 4° C.

Next, 6-(4'-carboxyphenyl)-3,8-bromoacetylamidyl-5-methylphenanthridinium chloride, (III) is prepared as follows. A 100 mg portion of 6-(-4'-carboxyphenyl)-3,8-diamino-5-methylphenanthridinium chloride (M-B 3492) (I) is dissolved in dimethylformamide (5 ml), 2.5M dimethylaminopyridine (7 ml) is added followed by addition of N-hydroxylsuccinimidyl ester of bromoacetic acid (II) (140 mg). The mixture is reacted for 10 minutes at room temperature to bromoacetylate the amino groups of (I), thereby forming compound III.

Formation of the tyramide of compound III, is as follows. N-hydroxysuccinimide (33 mg) is dissolved in the reaction mixture prepared above by heating to 70° C., then dicyclohexylcarbodiimide (61 mg) is added. This is reacted at 70° C. for 90 minutes, an additional amount (6 mg) of the carbodiimide is added and the reaction is continued for another 30 minutes. The mixture is cooled to 0° C. and the precipitated dicyclohexylurea is settled by centrifugation. The supernatant, containing 6-(-4'-N-hydroxylsuccinimidyl carboxy phenyl)-3,8-bis bromoacetamidyl-5-methylphenanthridinium chloride (IV) is recovered. A solution of tyramine [4-(2'-amino)ethylphenol] (1.0 g) in water (5 ml) is formed by bringing it to pH 7 by addition of concentrated HCl. This solution is added to the supernatant containing compound IV and reacted at room temperature for one hour. This mixture is then reduced to a red oil by evacuation at 60° C., and is then extracted with water to remove excess tyramine. Compound (VI) is then recrystalized from ethanol-acidified with HCl.

Azo coupling of the resulting intercalator to the activated glass surface is as follows. A glass coverslip derivatized as above, is transferred to cold (0° C.) 20 mM sodium phosphate buffer, pH 6.8 (1 ml) and the above dimethylformamide solution (5 ml), containing compound VI, is added. This mixture is reacted at 0° C. for one hour to form an azo linkage. The temperature is raised to room temperature overnight to hydrolyze the bromoacetyl groups. The light red coverslips are rinsed repeatedly with alcohol to remove uncoupled material and air dried.

Probe Preparation

The sequence of the probe prepared in accordance with this model experimental procedure is $(dT_3AAdU)_7$. A 5-hydroxy-DCTA is reacted with thiopropionic acid in a manner substantially identical with that described for the thiopropionic acid hydrazide in Example 3 of Stavrianopoulos. U.S. Pat. No. 4,707,440, supra. The disclosure of this patent is herein incorporated by reference.

Preparation of Sample for Assay

1) In a well of a four-well microscope slide, the sample is combined with, 2.0 M $NaPO_4$ buffer, probe, distilled water and formamide to make a solution of 150 microliters total volume in which:
    a) pH is 6.5–7.0
    b) sodium ion concentration is 100 millimolar,
    c) $T_m$ of desired probe-target hybrid is 42° C.,
    d) probe concentration is 70 nM (phosphate).
2) The well is covered with derivatized fused silica coverslip, derivatized slide down and heated to 95° C. to denature double helical regions of target.
3) Hybridization is carried out for 5 minutes at approximately 6° C. below the $T_m$ (37° C. for $(dT_3 AAdU)_7$) to form probe-target hybrids.
4) The sample is incubated at room temperature for five minutes to bind double-stranded DNA to coverslip by intercalation.
5) The solution is removed from the slide well and replaced with a wash buffer (as in step 1, except there is no probe). The sample is equilibrated at room temperature for 5 minutes.
6) The wash solution is removed. 100 microliters of solution 1.1 micromolar in energy donor and 150 millimolar in sodium phosphate (pH 6.8) is added and equilibrated for 5 minutes.
7) The coverslip is removed and excess solution is shaken off. The coverslip is mounted onto the sample delivery system.

Automated Assay

1) When using automated instrumentation in which a sample delivery system positions vessels, such as tubes or cuvettes, or analytical elements containing samples to be excited and to emit energy to be detected, the sample is automatically positioned for processing.
2) Step 1 above is repeated for each of the sample-containing analytical elements to be examined.
    For example, in a TRF laser fluorometer:
    a) laser pulses (337 nm nitrogen gas laser for psoralenamine energy donor, 405 nm diphenylstilbene dye laser for 9-aminoacridine energy donor).
    b) photodiode detects laser pulse intensity; this is digitized and transferred to array in computer memory.

c) 200 microseconds after laser pulse, photon counting begins at 620 nm. Photons from sample are counted for 1.024 milliseconds.

d) Photon count is transferred to computer temporary storage.

e) 45 milliseconds after laser fires, photons from sample are counted for a further 1.024 milliseconds. This is the dark count.

f) Dark count is transferred to computer. Difference between count in temporary store and dark count is stored in a second array in memory.

g) After 50 milliseconds elapse, cycle restarts at a), above.

3) User chooses whether to have computer calculate the average photon count per second of photon counting time by averaging numbers in the second array; or to normalize the count to unit laser output by dividing each number in the second array by the corresponding number in the first array. The results are reported to the operator by computer. The computer also calculates and reports the confidence level of the result for that sample.

What is claimed is:

1. A process for detecting the presence of a nucleic acid sequence of interest comprising:
    (a) providing:
        (i) an oligo- or polynucleotide which is specifically hybridizable with said nucleic acid sequence of interest, said oligo or polynucleotide comprising at least one lanthanide metal or at least one fluorophore, each acting as either an energy donor or an energy acceptor;
        (ii) a solid matrix having at least one surface to which is fixed or immobilized a first intercalator capable of capturing double-stranded nucleic acid, and
        (iii) a second intercalator, which may or may not comprise at least one fluorophore, said second intercalator or said fluorophore, each acting as either an energy donor or an energy acceptor;
    (b) forming a complex comprising:
        said oligo- or polynucleotide (i),
        said solid matrix (ii),
        said second intercalator (iii), and
        said nucleic acid sequence of interest if contained in said sample; and
    (c) detecting the presence of said nucleic acid sequence of interest by detecting any energy emitted from said energy acceptor.

2. The process according to claim 1, wherein in said providing step (a), the nucleic acid sequence of interest is present in single-stranded form or has been rendered at least partially single-stranded.

3. The process according to claim 1, wherein in said providing step (a), the double-stranded nucleic acid capturable by said first intercalator fixed or immobilized to the solid matrix (ii) is selected from the group consisting of double-stranded DNA, double-stranded RNA and DNA-RNA hybrids.

4. The process according to claim 1 wherein said forming step further comprises the step of separating any unhybridized oligo- or polynucleotide from said mixture.

5. The process according to claim 1, wherein in said providing step (a), the lanthanide metal (i) is selected from the group consisting of europium and terbium.

6. The process according to claim 5 wherein said lanthanide metal is chelated.

7. The process of claim 6 wherein said lanthanide chelate is bound to said oligo- or polynucleotide through a linkage group.

8. The process according to claim 1, wherein in said providing step (a), the first intercalator fixed or immobilized to the solid matrix (ii) is selected from the group consisting of phenanthridines and psoralenenamines.

9. A process for detecting the presence of a nucleic acid sequence of interest in a sample comprising:
    (a) providing a solid matrix having at least one surface to which is attached a first intercalator capable of capturing double-stranded nucleic acid;
    (b) contacting under hybridizable conditions said solid matrix with the sample suspected of containing said nucleic acid sequence of interest and an oligo- or polynucleotide which is specifically hybridizable therewith, said oligo or polynucleotide comprising at least one lanthanide metal or at least one fluorophore, each acting as either an energy donor or an energy acceptor, to form a complex which is captured by said solid matrix;
    (c) contacting said captured complex with a second intercalator, which may or may not comprise at least one fluorophore, said second intercalator or said fluorophore, each acting as either an energy donor or an energy acceptor, and
    (d) detecting the presence of said nucleic acid sequence of interest by detecting any energy emitted from said energy acceptor.

10. The process according to claim 9 wherein said nucleic acid sequence of interest is present in single-stranded form or has been rendered at least partially single-stranded.

11. The process according to claim 9 wherein the double-stranded nucleic acid capturable by said first intercalator is selected from the group consisting of double-stranded DNA, double-stranded RNA and DNA-RNA hybrids.

12. The process according to claim 9 further comprising the step of separating any unhybridized oligo- or polynucleotide from said complex.

13. The process according to claim 9 wherein said lanthanide metal is selected from the group consisting of europium and terbium.

14. The process according to claim 13 wherein said lanthanide metal is chelated.

15. The process of claim 14 wherein said lanthanide chelate is bound to said oligo- or polynucleotide through a linkage group.

16. The process of claim 9 wherein said first intercalator is selected from the group consisting of phenanthridines and psoralenamines.

17. A process for detecting the presence of a nucleic acid sequence of interest comprising:
    (a) contacting a sample suspected of containing said nucleic acid sequence of interest with an oligo- or polynucleotide hybridizable therewith to form a hybrid, said oligo- or polynucleotide having directly or indirectly bound thereto a lanthanide metal or a fluorophore, each independently acting as either an energy donor or an energy acceptor;
    (b) contacting said hybrid with a solid matrix having at least one surface to which is attached a first intercalator capable of capturing double-stranded nucleic acid;
    (c) permitting capture of said hybrid to form a complex;
    (d) contacting said complex with a second intercalator, which may or may not comprise at least one fluorophore, said second intercalator or said fluorophore, each acting as either an energy donor or an energy acceptor; and
    (e) detecting the presence of said nucleic acid sequence of interest by detecting any energy emitted from said energy acceptor.

18. The process according to claim 17, wherein said nucleic acid sequence of interest is present in single-stranded form or has been rendered at least partially single-stranded.

19. The process according to claim 17, wherein the double-stranded nucleic acid capturable by the first intercalator in said contacting step (b) is selected from the group consisting of double-stranded DNA, double-stranded RNA and DNA-RNA hybrids.

20. The process according to claim 17, further comprising the step of separating prior to said detecting step (e) any unhybridized oligo- or polynucleotide from any complex that is formed.

21. The process according to claim 17, wherein said lanthanide metal in step (a) is selected from the group consisting of europium and terbium.

22. The process according to claim 21, wherein said lanthanide metal in step (a) is chelated.

23. The process of claim 22, wherein said lanthanide chelate is bound to said oligo- or polynucleotide through a linkage group.

24. The process of claim 17, wherein said first intercalator attached to the solid matrix in said contacting step (b) is selected from the group consisting of phenanthridines and psoralenamines.

* * * * *